US006194378B1

(12) United States Patent
Clark et al.

(10) Patent No.: US 6,194,378 B1
(45) Date of Patent: *Feb. 27, 2001

(54) FIBRONECTIN PEPTIDES-BASED EXTRACELLULAR MATRIX FOR WOUND HEALING

(75) Inventors: Richard A. Clark, Poquott, NY (US); Doris Greiling, Deal (GB)

(73) Assignee: The Research Foundation of State University of New York, Albany, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/025,622

(22) Filed: Feb. 18, 1998

(51) Int. Cl.$^7$ .................................................. A61K 38/00
(52) U.S. Cl. .................... 514/2; 514/13; 514/14; 514/15; 514/16; 514/17; 514/18; 530/326; 530/327; 530/328; 530/329; 530/330; 530/331; 530/381
(58) Field of Search .................... 514/2, 13–18; 530/326–331, 381

(56) References Cited

U.S. PATENT DOCUMENTS

| | | |
|---|---|---|
| 4,453,939 | 6/1984 | Zimmerman et al. . |
| 4,589,881 | 5/1986 | Pierschbacher et al. . |
| 4,950,483 | 8/1990 | Ksander et al. . |
| 4,970,298 | 11/1990 | Silver et al. . |
| 4,981,841 | 1/1991 | Gibson . |
| 5,024,841 | 6/1991 | Chu et al. . |
| 5,198,423 * | 3/1993 | Taguchi et al. ......................... 514/12 |
| 5,294,551 * | 3/1994 | Furcht et al. ......................... 435/402 |
| 5,453,489 | 9/1995 | Ruoslahti et al. . |
| 5,489,304 | 2/1996 | Orgill et al. . |
| 5,591,719 * | 1/1997 | Furcht et al. ......................... 514/13 |
| 5,604,200 * | 2/1997 | Taylor-McCord ......................... 514/8 |
| 5,616,568 | 4/1997 | Pouyani et al. . |
| 5,631,011 | 5/1997 | Wadstrom . |
| 5,641,483 | 6/1997 | Beaulieu . |
| 5,652,347 | 7/1997 | Pouyani et al. . |
| 5,654,267 * | 8/1997 | Vuori et al. ......................... 514/2 |
| 5,679,320 * | 10/1997 | Vogel et al. ......................... 424/1.69 |
| 5,958,874 * | 9/1999 | Clark et al. ......................... 514/2 |

OTHER PUBLICATIONS

HCAPLUS on 124:333140, Kuroyanasi, T., JP 08073373, 5 pp., 1996.*
Bartold et al., J Periodont Res 31:205–216 (1996).
Bell et al., Proc Natl Acad Sci USA 76(3):1274–1278 (1979).
Cameron et al., Invest Ophth & Vis Sci 32(10):2766–2773 (1991).
Clark et al., J. Clin Invest 84:1036–1040 (1989).
DuBlois et al., Biomaterials 15(9):665–672 (1994).
De Vries et al., Lab Invest 73(4):532–540 (1995).
Greiling et al., J Cell Sci 110:861–870 (1997).
Henke et al., J. Clin Invest 97(11):2541–2552 (1996).
Kartha et al., J Clin Invest 90:288–292 (1992).
Kim et al., Lab Invest 71(3):401–408 (1994).
Kishida et al., Biomaterials 13(13):924–930 (1992).
Knox et al., J Cell Phys 132:501–508 (1987).
Kratz et al., Scand J Plast Reconstr Hand Surg 31:119–123 (1997).
Lamme et al., J. Histo & Cytoch 44(11):1311–1322 (1996).
Middelkoop et al., Cell Tissue Res 280:447–453 (1995).
Nakamura et al., Exp Eye Res 64:1043–1050 (1997).
Nicosia et al., Am J Path 145(5):1023–1029 (1994).
Nicosia et al., Am J Path 128(1):78–90 (1987).
Patel et al., Inter Immun 7(2):277–286 (1995).
Schor et al., J Cell Sci 109:2581–2590 (1996).
Sponsel et al., Am J Physiol 267:F257–F264 (1994).
Steed et al., Diabetes Care 18(1):39–46 (1995).
Tomasek et al., The Anat Record 234:153–160 (1992).
Yamada et al., Scan J Plast Reconstr Hand Surg 29:211–219 (1995).

* cited by examiner

Primary Examiner—Dwayne C. Jones
Assistant Examiner—C. Delacroix-Muirheid
(74) Attorney, Agent, or Firm—Braman & Rogalskyj, LLP

(57) ABSTRACT

The invention provides an extracellular matrix for wound healing comprising peptides from two or more fibronectin domains in a backbone matrix. In one embodiment, the subject invention provides a hyaluronic acid backbone derivatized with the minimal FN sequences that are optimal for tissue cell recruitment. These constructs can be used to accelerate the healing of acute gaping cutaneous wounds and chronic cutaneous ulcers. The invention thus further provides a method of enhancing wound healing which comprises applying the extracellular matrix to a wound.

21 Claims, 7 Drawing Sheets

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 3 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Arg Gly Asp
1

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Pro His Ser Arg Asn
1               5

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Glu Ile Leu Asp Val Pro Ser Thr
1               5

(2) INFORMATION FOR SEQ ID NO:4:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Asp Glu Leu Pro Gln Leu Val Thr Leu Pro His Pro Asn Leu His Gly
1               5                   10                  15
Pro Glu Ile Leu Asp Val Pro Ser Thr
            20                  25

(2) INFORMATION FOR SEQ ID NO:5:

(i) SEQUENCE CHARACTERISTICS:
        (A) LENGTH: 20 amino acids

```
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Gly Glu Glu Ile Gln Ile Gly His Ile Pro Arg Glu Asp Val Asp Tyr
1               5                  10                  15

His Leu Tyr Pro
            20

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Tyr Glu Lys Pro Gly Ser Pro Arg Arg Glu Val Val Pro Arg Pro Arg
1               5                  10                  15

Gly Val (2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Lys Asn Asn Gln Lys Ser Glu Pro Leu Ile Gly Arg Lys Lys Thr
1               5                  10                  15

(2) INFORMATION FOR SEQ ID NO:8:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Tyr Arg Val Arg Val Thr Pro Lys Glu Lys Thr Gly Pro Met Lys Glu
1               5                  10                  15

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Ser Pro Pro Arg Arg Ala Arg Val Thr
1               5
```

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Trp Gln Pro Pro Arg Ala Arg Ile
1             5

(2) INFORMATION FOR SEQ ID NO:11:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Val Val Ile Asp Ala Ser Thr Ala Ile Asp Ala Pro Ser Asn Leu Arg
1         5              10             15

Phe Leu Ala (2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Glu Ile Leu Glu Val Pro Ser Thr
1         5

FIBRONECTIN PEPTIDES-BASED EXTRACELLULAR MATRIX FOR WOUND HEALING

The subject matter of this application was made with support from the United States Government under National Institutes of Health Grant No. AG 101143-12.

FIELD OF THE INVENTION

The subject invention is directed to an extracellular matrix for wound healing and to a method of enhancing wound healing using the extracellular matrix.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

It is estimated that in 1992 (US), 35.2 million wounds required major therapeutic intervention (Medical Data International, Inc. 1993). Surgical incisional wounds are performed with aseptic technique, and are closed by primary intention. Most repair and heal uneventfully. Many traumatic wounds and cancer extirpations, however, must be left open to heal by secondary intention. Furthermore, chronic wounds have significant tissue necrosis and fail to heal by secondary intention. It is estimated that 5.5 million people in the US have chronic, nonhealing wounds and that their prevalence is increasing secondary to the increase in age-related diseases, the increase in Acquired-immune Deficiency Syndrome (AIDS), and the increase of radiation wounds secondary to cancer intervention. In the US approximately 1.5–2.5 million people have venous leg ulcers; 300,000–500,000, diabetic ulcers; and 2.5–3.5 million, pressure ulcers (Callam et al. 1987; Phillips and Dover 1991; Lees and Lambert 1992; Lindholm et al. 1992). These acute and chronic open wounds require long-term care and procedures that include skin grafting and tissue flaps, debridement, frequent dressing changes and administration of pain medications. This care is costly and labor intensive. Furthermore, these wounds have a severe impact on the patients' quality of life. The chronic dermal ulcerations can cost as much as $40,000 each to heal and more disappointing is that 50% reappear within 18 months of healing. Chronic dermal ulcers are also associated with mortality. As many as 21% of patients in intermediate-care facilities with pressure ulcers die (Bergstrom et al. 1994).

Although multiple millions of dollars have been spent on the development of numerous recombinant growth factors (Abraham and Klagsbrun 1996; Heldin and Westermark 1996; Nanney and King 1996; Roberts and Sporn 1996) and organotypic skin replacements (Boyce et al. 1995) for use in open wounds over the past decade, the evidence of cost-effective benefit is meager thus far (Brown et al. 1989; Robson et al. 1992a; Robson et al. 1992b; Phillips et al. 1993).

Many attempts have been made to produce a composition which can be used to facilitate wound repair. Many of these compositions involve collagen as a component. U.S. Pat. Nos. 4,950,483 and 5,024,841 each discuss the usefulness of collagen implants as wound healing matrices. U.S. Pat. No. 4,453,939 discusses a wound healing composition of collagen with a fibrinogen component and a thrombin component, and optionally fibronectin. U.S. Pat. No. 4,970,298 discusses the usefulness of a biodegradable collagen matrix (of collagen, hyaluronic acid, and fibronectin) for wound healing. Yamada et al. (1995) disclose an allogeneic cultured dermal substitute that is prepared by plating fibroblasts onto a spongy collagen matrix and then culturing for 7 to 10 days. Devries et al. (1995) disclose a collagen/alpha-elastin hydrolysate matrix that can be seeded with a stromal-vascular-fraction of adipose tissue. Lamme et al. (1996) disclose a dermal matrix substitute of collagen coated with elastin hydrolysate. U.S. Pat. No. 5,489,304 and Ellis and Yannas (1996) each disclose a collagen-glycosaminoglycan matrix.

There are also numerous compositions which involve hyaluronic acid (HA) as a component. Ortonne (1996), Borgognoni et al. (1996), and Nakamura et al. (1997) each discuss the usefulness of HA for wound healing. In Nakamura et al. (1997), the HA was combined with chondroitin sulfate in one series of experiments. In U.S. Pat. No. 5,604,200, medical grade HA and tissue culture grade plasma fibronectin were used in combination with calcium, phosphate, uric acid, urea, sodium, potassium, chloride and magnesium to create a moist healing environment that simulates the fetal in utero wound healing matrix. U.S. Pat. No. 5,631,011 discloses a composition of HA and fibrin or fibrinogen.

Various other compositions have also been explored for their wound healing capabilities. Kratz et al. (1997) used a gel of heparin ionically linked to chitosan. Bartold and Raben (1996) studied platelet-derived growth factor (PDGF). Henke et al. (1996) disclosed that chondroitin sulfate proteoglycan mediated cell migration on fibrinogen and invasion into a fibrin matrix, while Nakamura et al. (1997) concluded that chondroitin sulfate did not affect wound closure in a corneal epithelial wound. Henke et al. (1996) also disclosed that an anti-CD44 antibody blocked endothelial cell migration on fibrinogen. U.S. Pat. No. 5,641,483 discloses topical gel and cream formulations containing human plasma fibronectin for healing of cutaneous wounds. Schultz et al. (1992) disclose a composition of epidermal growth factor (EGF), fibronectin, a synthetic collagenase inhibitor, and Aprotinin.

Various studies involving fibronectin (FN) and/or particular fibronectin peptides and wound healing have also been reported. Many of these studies involve the RGD sequence, part of the cell binding domain of FN (see Schor et al. 1996; Steed et al. 1995; Sponsel et al. 1994; Kartha and Toback 1992; Kishida et al. 1992). Schor et al. (1996) disclose that only the gelatin binding domain of FN (GBD) stimulates fibroblast migration into a 3-D matrix of native type I collagen fibrils at femtomolar concentrations; whereas peptides of the other FN functional domains do not stimulate fibroblast migration in this assay at femtomolar to nanomolar concentrations. Schor et al. (1996) also disclose that the RGDS-containing cell binding domain of FN does, however, stimulate fibroblast migration in the transmembrane (or "Boyden chamber") assay. Steed et al. (1995) disclose that the RGD peptide matrix (known as Argidene Gel™ or as Telio-Derm Gel™) promoted wound healing. On the contrary, Sponsel et al. (1994) disclose that an RGD peptide impaired healing of a mechanical wound made in a confluent monolayer of one epithelial cell line. Kartha and Toback (1992) also concluded that an RGDS peptide completely inhibited cell migration into a wound area. Kishida et al. (1992), however, disclose that an RGD-albumin conjugate adsorbed onto a polyurethane sponge exhibited tissue ingrowth-promoting activity.

Other portions of FN have also been studied for wound healing activity. U.S. Pat. No. 5,198,423 studied the effects of a polypeptide containing a cell binding domain and a heparin binding domain of FN on wound healing. U.S. Pat. No. 4,589,881 studied the effects of a 108 aa polypeptide fragment of FN on wound healing, as well as a biologically active fragment thereof. Sponsel et al. (1994) studied the effect of the tetrapeptide REDV and the peptide LDVPS on wound healing.

The severity of the problem of chronic, nonhealing wounds dictates that continual efforts be made to define new and more effective matrices and methods for facilitating wound healing.

SUMMARY OF THE INVENTION

This need is met by the subject invention which provides an extracellular matrix for enhancing wound healing. The extracellular matrix comprises peptides from two or more fibronectin domains in a backbone matrix. The extracellular matrix facilitates wound healing by providing an environment that intrinsically recruits new tissue cells to the wound site.

A method of enhancing wound healing is also provided by the subject invention. The method comprises applying the extracellular matrix as so defined to a wound.

Using an in vitro model of cell movement across 3-dimensional extracellular matrix boundaries that simulates early wound repair (Greiling and Clark 1997), the experiments related to the subject invention established that multiple domains of FN were required for fibroblast movement. In one embodiment, the subject invention provides a hyaluronic acid backbone derivatized with the minimal FN sequences that are optimal for tissue cell recruitment. These constructs can be used to accelerate the healing of acute gaping cutaneous wounds and chronic cutaneous ulcers.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION OF THE INVENTION

The subject invention provides an extracellular matrix for wound healing which comprises peptides from two or more fibronectin domains in a backbone matrix. As used herein, an "extracellular matrix" refers to a scaffold in the cell's external environment with which the cells may interact via specific cell surface receptors. As further used herein, a "wound" is intended to include both acute and chronic dermal wounds including, for example, surgical incisional wounds, traumatic wounds, cancer extirpations, radiation wounds, venous leg ulcers, diabetic ulcers, and pressure ulcers.

The extracellular matrix according to the subject invention comprises peptides from two or more fibronectin domains in a backbone matrix. These components are necessary for the subject extracellular matrix to enhance (e.g. improve, increase) wound healing, although additional components may also be included in the extracellular matrix. These additional components, such as platelet-derived growth factor as discussed below, may further enhance the beneficial effects of the extracellular matrix on wound healing.

Enhancement (e.g. improvement, increasing) of wound healing refers to the traditional sense of wound healing where clean closure of the wound occurs. Since naturally occurring wound healing involves the movement of fibroblasts into the wound site, enhancement of wound healing can be assayed in vitro using the model for cell transmigration provided in copending, co-assigned U.S. Ser. No. 08/723,789, filed Sep. 30, 1996 (the contents of which are incorporated by reference herein). Briefly, the model provides a contracted collagen gel containing fibroblasts surrounded by a fibrin gel (see FIG. 1). When the extracellular matrix of the subject invention replaces or is added to the fibrin gel, fibroblast movement from the collagen gel into the extracellular matrix or modified fibrin gel is enhanced compared to movement into the "gold standard" fibrin gel.

Figure 2:
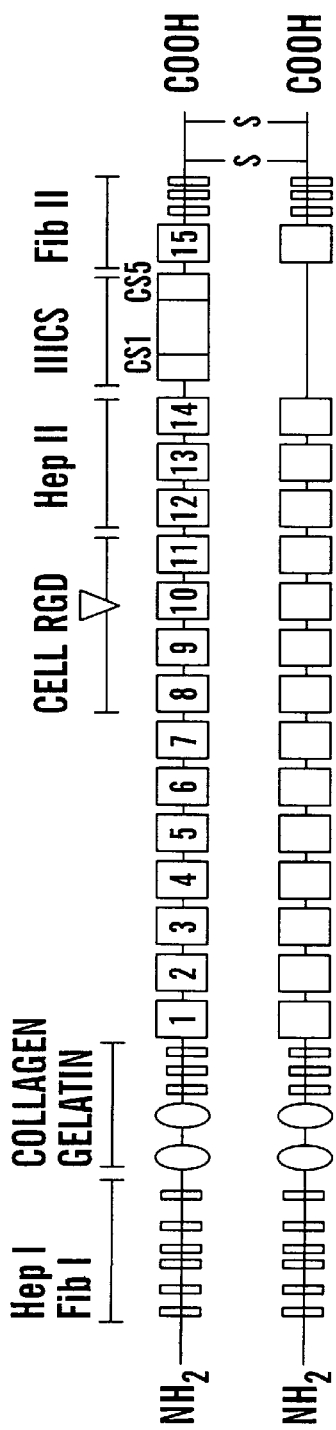
FIG. 2 illustrates the general structure of fibronectin, showing the number and relative positions of the basic functional domains.

The extracellular matrix of the subject invention comprises peptides from two or more fibronectin domains in a backbone matrix. Fibronectin is a multi-domain, multifunctional cell adhesion protein found in blood and in a variety of tissue extracellular matrices (Yamada and Clark 1996). Although encoded by only a single gene, FNs exist in a number of variant forms that differ in sequence at three general regions of alternative splicing of its precursor mRNA. Some of this alternative splicing involves cell adhesion sequences, thereby providing a post-transcriptional mechanism for potentially regulating cell interaction. Nevertheless, all FN molecules appear to consist of the same basic functional domains. As shown in FIG. 2, these domains include two heparin binding domains, Hep I and Hep II; two fibrin binding domains, Fib I and Fib II; a collagen or gelatin binding domain; a cell-binding domain; and a variably splice IIICS domain, which contains within it CS1 and CS5 subdomains. Each domain is composed of FN repeats denoted as thin rectangles for the type 1 repeats, ovals for the type 2 repeats, and wide rectangles for the type 3 repeats.

The peptides from two or more fibronectin domains are therefore selected from the domains indicated above. Suitable peptides include those from the cell binding domain (such as peptides including the amino acid sequence SEQ ID NO:1: and peptides including the amino acid sequence SEQ ID NO:2:), the IIICS domain (such as peptides including the amino acid sequence SEQ ID NO:3 which is a truncated CS1 peptide; or the peptide designated CS1 and having an amino acid sequence as shown in SEQ ID NO:4; or the peptide designated CS5 and having an amino acid sequence as shown in SEQ ID NO:5), and the heparin II binding domain (such as the peptide designated H-I and having an amino acid sequence as shown in SEQ ID NO:6; or the peptide designated H-II and having an amino acid sequence as shown in SEQ ID NO:7; or the peptide designated H-III and having an amino acid sequence as shown in SEQ ID NO:8; or the peptide designated H-IV and having an amino acid sequence as shown in SEQ ID NO:9; or the peptide designated H-V and having an amino acid sequence as shown in SEQ ID NO:10; or the peptide having an amino acid sequence as shown in SEQ ID No:11 {a COOH-terminal HepII peptide that binds α4β1}). Preferably, the two or more fibronectin domains according to the subject invention are selected from the type III repeats (the wide rectangles in FIG. 2) or the IIICS region.

Having identified the peptides from two or more fibronectin domains that will be added to a backbone matrix, it should be readily apparent that these peptides can be made by any suitable means; for example, the peptides can be constructed using peptide synthesis technology (synthetic peptides), or cut out of a naturally occurring fibronectin molecule using proteolytic enzymes. Small peptides will probably need to be conjugated (covalently attached) to the backbone matrix but non-covalent delivery systems may also be appropriate (for example, the peptides may be held within the backbone matrix by affinity interactions).

As further used herein, a "backbone matrix" refers to natural extracellular matrices as well as biocompatible synthetic polymers. These backbone matrices provide the scaffold of the extracellular matrix and when the peptides of two or more fibronectin domains are in the backbone matrix, cells can move around on the scaffold. According to this invention, the peptides are provided as relatively small molecules and therefore must be held within to the backbone matrix or else the peptides would diffuse away. The backbone matrix thus provides the structure to which the peptides can be conjugated or non-covalently retained.

There are numerous examples of backbone matrices suitable for use in the subject invention. These examples include fibrin, hyaluronic acid, polyethylene glycol, poly-L-glycol, and poly-L-lactate. Hyaluronic acid is commercially available as a dry (for example, lyophilized) powder, and can be reconstituted to a hyaluronic acid gel (in accordance with manufacturer's suggestions) for use in the subject invention. Depending upon the viscosity desired, a hyaluronic acid gel having about 5 milligrams to about 50 milligrams of hyaluronic acid per milliliter of reconstituting solution can be used. At 5 milligrams/milliliter, the hyaluronic acid gel will be more liquid, and at 50 milligrams/milliliter the hyaluronic acid gel will become more viscous and less easy to manipulate. The use of the gel will, in part, dictate the desired viscosity. If the extracellular matrix can be "poured" into and contained in a wound area, then a more liquid form of the hyaluronic acid gel will be satisfactory. If the extracellular matrix is "spread" over and/or into a wound area, then a more viscous form of the hyaluronic acid gel will be desirable. In either case, a dressing of some form will often cover the applied extracellular matrix to help prevent contamination and infection of the wound. It should be readily apparent that the extracellular matrix itself (and each of its components) must be sterile (free of biological and/or chemical contamination) to also prevent contamination and infection of the wound.

Preferably, the hyaluronic acid gel is provided as a gel having about 20 milligrams of dry hyaluronic acid per milliliter of reconstituting solution. Suitable reconstituting solutions include, for example, sterile distilled water, sterile phosphate buffered saline (PBS), or a cell culture medium.

As used herein, "hyaluronic acid" is intended to include the various forms of hyaluronic acid (HA) known in the art. These various forms include HA chemically modified (such as by cross-linking) to vary its resorbtion capacity and/or its ability to be degraded. Optimal HA formulations will be resorbable in a few days to a week.

The peptides can be conjugated to the backbone matrix using techniques known in the art. Such techniques include the use of a heterobifunctional crosslinking reagent. In some embodiments, it may be desirable to alter the amino terminal amino acid of the peptide to allow conjugation to the backbone matrix. U.S. Pat. Nos. 5,652,347 and 5,616,568 disclose methodology for the functional derivatization of hyaluronic acid using dihydrazide. The contents of each of these patents is incorporated herein by reference.

The extracellular matrix can further comprise other components which further enhance the cell migration effect of the matrix. Such additional components include, for example, platelet derived growth factor.

The invention further provides a method of enhancing wound healing which comprises applying the extracellular matrix (as described herein) to a wound. As discussed above, the method of applying the extracellular matrix to the wound may vary depending on the type and location of the wound as well as the viscosity of the extracellular matrix. Preferably, the extracellular matrix is viscous enough to be "spread" over the wound and will not run off after application.

MATERIALS AND METHODS

Normal Human Dermal Fibroblasts

Primary cultures of human adult dermal fibroblasts, acquired from Marcia Simon (Living Skin Bank, SUNY at Stony Brook), the ATCC (Bethesda, Md.), or the NIA (Bethesda, Md.), are cultured in Dulbecco's modified Eagle's medium (DMEM, Life Technologies) containing 42 mM sodium bicarbonate and supplemented with 100 U/ml penicillin, 100 µg/ml streptomycin, and 10% fetal bovine serum (FBS, HyClone, Logan, Utah), at 37° C. and 5% $CO_2$/95% air in a humidified atmosphere. The cells are used between passages 4 and 12.

Fibroblast Migration Assays: Transmigration from Organotypic Collagen Gel Constructs into Fibrin/Fibronectin Gels or Outmigration over Protein Coated Surfaces Preparation of Floating, Contracted Collagen Gels Fibroblast cultures at 80% confluence are harvested by treatment with 0.05% trypsin/0.01% EDTA. Trypsin is inactivated by addition of soy bean trypsin inhibitor in PBS containing 0.2% BSA. The cells are washed twice with DMEM+2% BSA and resuspended at a concentration of $1 \times 10^6$ cells/ml. The fibroblasts are mixed with neutralized collagen (Vitrogen 100, Celtrix Labs., Santa Clara, Calif.), 2% BSA, 30 ng/ml PDGF-BB, 30 µg/ml fibronectin, and concentrated DMEM so that the final concentration of DMEM and sodium bicarbonate is 1x. 600 µl of the cell mixture is added to the wells of a 24-well tissue culture plate, which has been precoated with 2% BSA. The collagen is allowed to polymerize at 37° C. The final concentration of collagen is 1.8 mg/ml and each gel contains $6 \times 10^4$ cells. After two hours incubation, the gels are gently detached from the plastic surface to allow contraction with the addition of 0.5 ml DMEM+2% BSA and 30 ng/ml PDGF-BB per well. The gels are incubated overnight at 37° C. in 100% humidity, 5% $CO_2$ and 95% air.

Preparation of Protein Coated Wells

Fibronectin, its fragments or recombinant domains were diluted with concentrated DMEM to the appropriate concentration. Aliquots of 450 µl protein solution are added to the wells of 24-well tissue culture plates (Becton-Dickinson, Lincoln Park, N.J.). After a 2 hour incubation at 37° C. in 5% $CO_2$, plates were dried overnight at room temperature under sterile conditions.

Preparation of Two-dimensional Outmigration Model

Plates coated with dried proteins were washed once with PBS and incubated with 2% BSA for 1 hour at 37° C. to block nonspecific binding sites. After washing the plates three times with PBS, contracted-collagen gel organotypic constructs were attached to the coated plates. DMEM, 2% BSA and 30 ng/ml PDGF-BB was added to assay plates so that the medium was level with the top of the collagen gel.

Preparation of Three-dimensional Transmigration Model

For preparation of "gold standard" transmigration assays containing a dermal organotypic construct surrounded by a fibrin clot as previously described (Greiling and Clark 1997), dried fibrin fibril-coated dishes are washed once with PBS and fibroblast-contracted collagen gels are placed on the surface. Fibrinogen, at a final concentration of 300 μg/ml, is mixed with DMEM and 1.0 U/ml thrombin, added to the wells so that the solution is level with the top of the collagen gel, and allowed to clot at room temperature for 30 min. When needed, other supplements such as 30 ng/ml PDGF-BB are added to the mixture. For HA 3-dimensional transmigration, wells are coated overnight at 37° C. with an appropriate solution of HA. The next day a fibroblast-contracted collagen gel is placed on the HA-coated well in DMEM, with or without 30 ng/ml PDGF-BB, is added so that the solution is level with the top of the collagen gels. All migration assays are quantified after a 24 hour incubation at 37° C. in 100% humidity, 5% $CO_2$ and 95% air.

Evaluation of Cell Migration

The number of migrated cells was quantified under a Nikon inverted phase microscope by visually counting identifiable cell nuclei located outside of the contracted collagen gel in the fibrin gel (transmigration assay) or on the matrix (outmigration assay). Within a given experiment each condition was run in triplicate and means ±SD calculated. All experiments were repeated at least three times. Statistical differences among conditions can be determined by ANOVA.

Fibroblast Adhesion Assay

Assay plates are prepared as described under fibroblast migration assays. The assay for measuring fibroblast adhesion to matrix proteins are performed essentially as described (Gailit et al. 1993) except that the cell concentration is lowered to 100,000 cells/ml or 10,000 cells/well. Cells are allowed to attach for 60 min at 37° C. before the unattached cells are washed away and the attached cells fixed with 2% glutaraldehyde. After fixation, attached cells are air dried at room temperature and then 100 ml of 0.1% crystal violet in 0.2 M boric acid, pH 9, is added to each well and the microtiter plate shaken at 600 rpm on a plate mixer for 20 minutes. (The staining solution is prepared fresh from a stock solution of 5% crystal violet in 20% methanol.) Excess stain is removed by three washes with water. The stained cells are again air dried before the crystal violet is solubilized by adding 100 ml of 10% acetic acid to each well and then shaking the plate at 600 rpm for 20 minutes. The absorbance at 590 nm is measured with a dual wavelength microtiter plate reader (THERMOmax, Molecular Devices, Menlo Park, Calif.) and the reading corrected for light scattering by subtraction of the absorbance at 450 nm.

EXAMPLE I

Assay of Wound Healing

Figure 1:
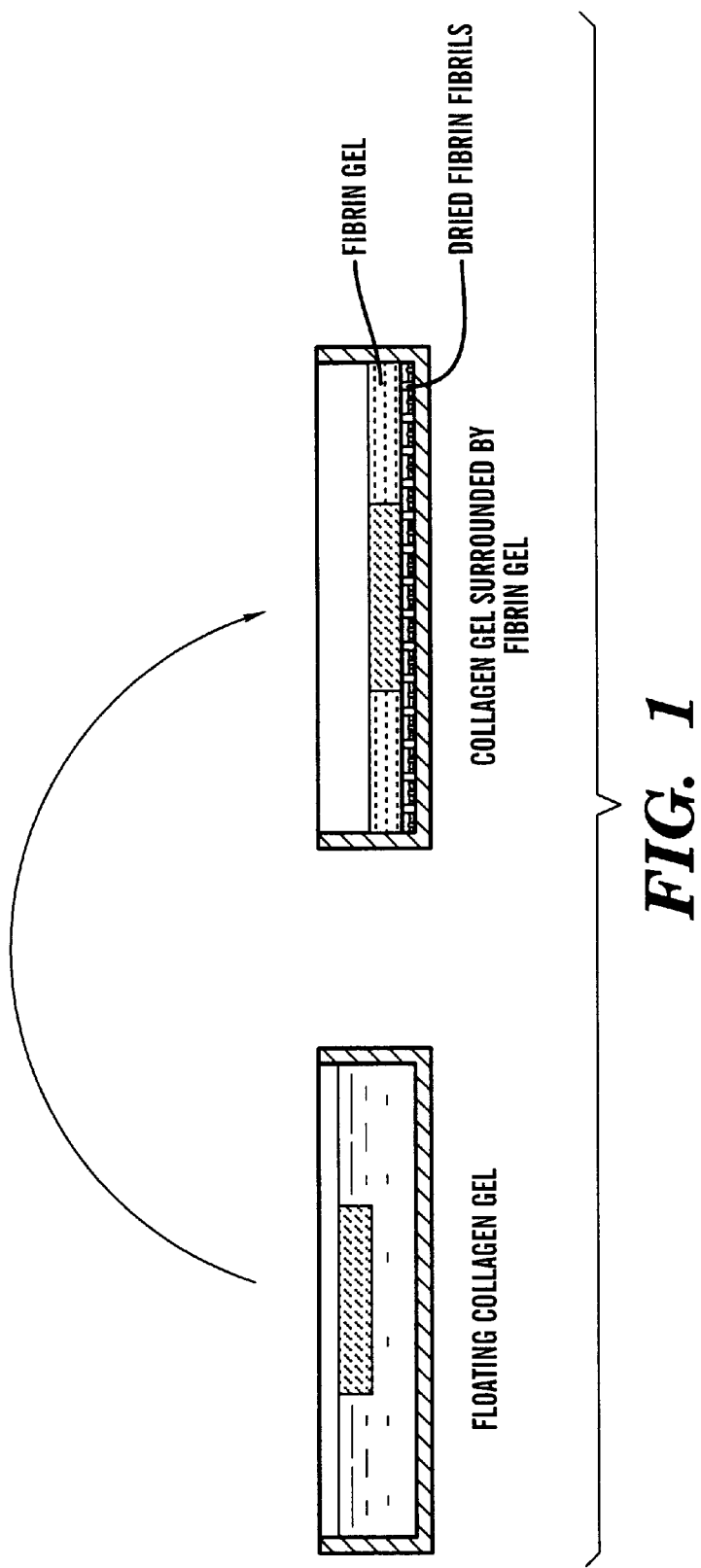
FIG. 1 illustrates the in vitro model for assaying cell transmigration from a collagen gel into a fibrin gel.

The extracellular matrix of the present invention was tested by use of the in vitro model as described in U.S. patent application Ser. No. 08/723,789, which is hereby incorporated by reference. The basis of the in vitro model is a contracted collagen gel containing fibroblasts which acquire a tissue-like phenotype within the collagen matrix. Surrounding the collagen gel, or dermal equivalent, with a fibrin clot produces a simple inside-outside model of the early cutaneous wound (FIG. 1). Without an added stimulus, no more than a few of the normal adult human dermal fibroblasts within the collagen gel would migrate into the fibrin gel. However, the transmigration of fibroblasts from the collagen gel into the fibrin gel is enhanced by the replacement of the fibrin gel with the extracellular matrix of the subject invention or by the addition of the extracellular matrix to the fibrin gel, since the extracellular matrix facilitates cell movement thereby enhancing wound healing.

EXAMPLE II

Figure 10A:
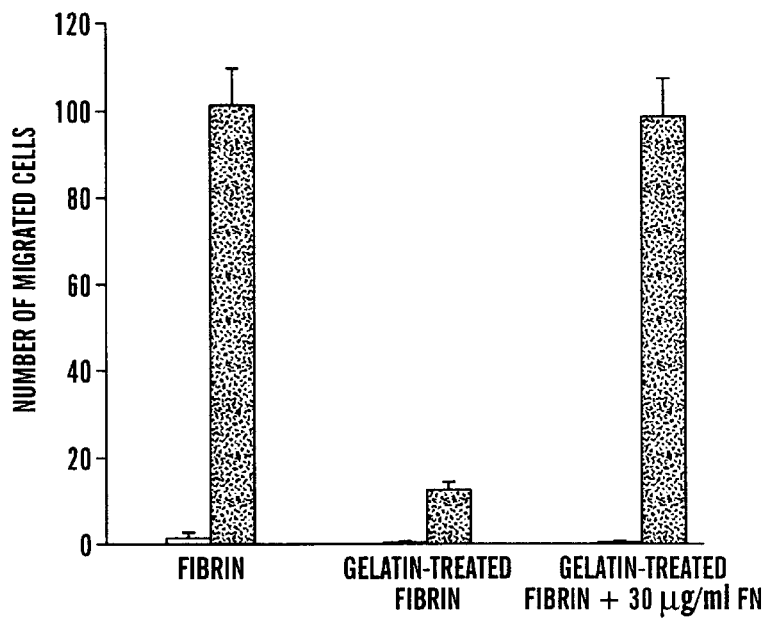
FIGS. 10A–10B illustrate the requirement of fibronectin for transmigration.

Fibronectin (FN) is required for fibroblast migration through both fibrin clots and hyaluronic acid (HA) gels. Initially, experiments were conducted to determine whether FN, either in a fibrin gel or in a collagen gel, is required for fibroblast transmigration. To do this, FN was selectively removed from each matrix material. First, residual FN was removed from the fibrinogen preparation by affinity chromatography on gelatin. After removal of FN, fibroblast transmigration into the fibrin clot was decreased by about 80% (FIG. 10A). Transmigration could be restored by the addition of FN to the fibrin gel. Optimal cell movement was observed with 30 μg/ml, a FN:fibrinogen ratio of 1:10, the physiological plasma ratio. In FIG. 10A, migration induced by 30 ng/ml PDGF-BB (shaded bars; open bars: 0 ng/ml PDGF) was measured under the usual assay conditions. The fibrinogen preparation used to form the fibrin gel was untreated (left), treated with gelatin-Sepharose to remove FN (center), or treated with gelatin-Sepharose and then supplemented with 30 μg/ml FN (right).

Figure 10B:
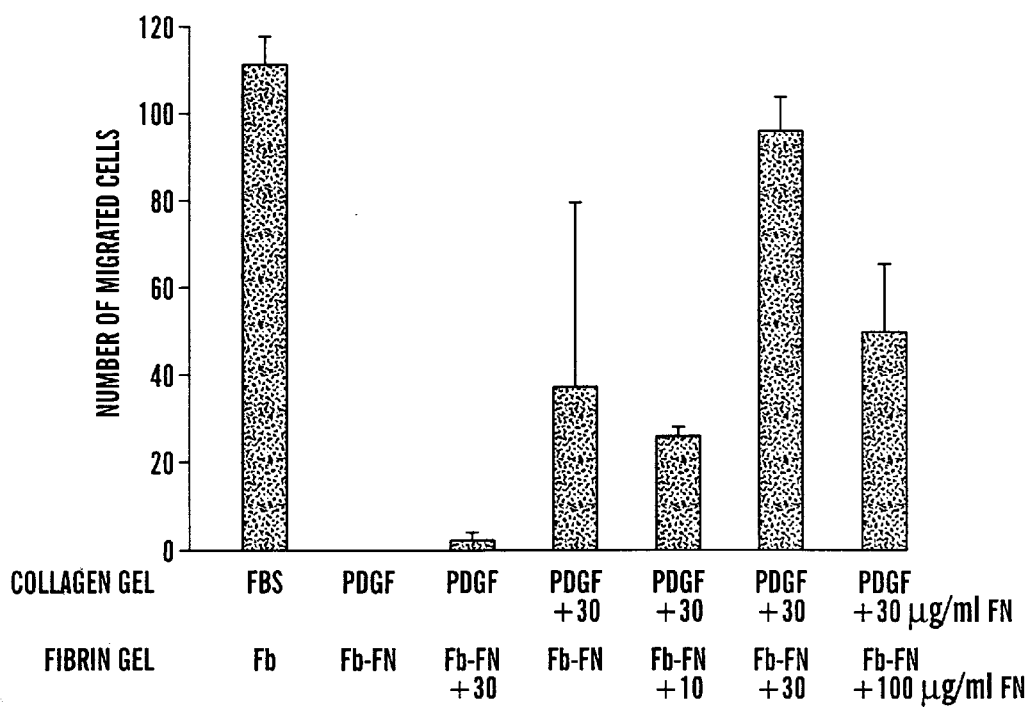

Second, exogenous FN was excluded from the collagen gel by omitting serum and substituting PDGF-BB, which is equally effective at stimulating fibroblast-driven collagen gel contraction. In experiments with FN-free collagen gels no transmigration occurred (FIG. 10B). Transmigration was only observed when FN was present in both the collagen gel and the fibrin gel; 30 μg/ml FN in each gel seemed the most effective. In FIG. 10B, migration induced by 30 ng/ml PDGF-BB (shaded bars) was measured under modified assay conditions. Contraction of the collagen gel was stimulated with serum as usual (FBS) or with 30 ng/ml PDGF-BB (PDGF). The fibrinogen preparation used to form the fibrin gel was untreated (Fb), treated with gelatin-Sepharose to remove FN (Fb-FN), or treated with gelatin-Sepharose and then supplemented with 10, 30, or 100 μg/ml FN. The inclusion of 30 μg/ml FN in the collagen gel and in the fibrin gel restored transmigration to a normal level.

Figure 3:
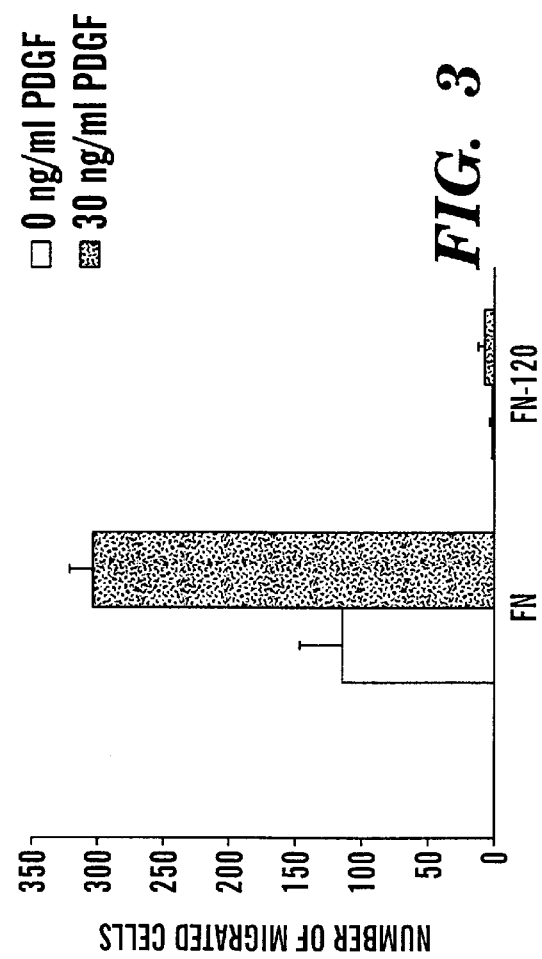
FIG. 3 illustrates the effect on cell migration of FN and FN-120 with or without PDGF.

Having established that FN is required for fibroblast migration, the FN domains necessary for migration were next examined. In the first experiment focused on the specific sequences of the FN molecule necessary for migration of fibroblasts, assay wells were coated with 120 nmol/l of either intact FN (FN) or the 120 kDa fragment of FN (FN-120). The FN-120 fragment was isolated from a chymotrypsin digest as previously described (Wikner and Clark 1988). FN-120 contains the RGDS cell-binding domain, but lacks the Hep II and IIICS domains (see FIG. 4). Surprisingly, although FN-120 promotes 70% adhesion of fibroblasts compared to intact FN, it does not allow migration (FIG. 3). Reduction and alkylation of FN dimer to the monomeric state did not affect its ability to mediate either adhesion or migration.

Figure 4:
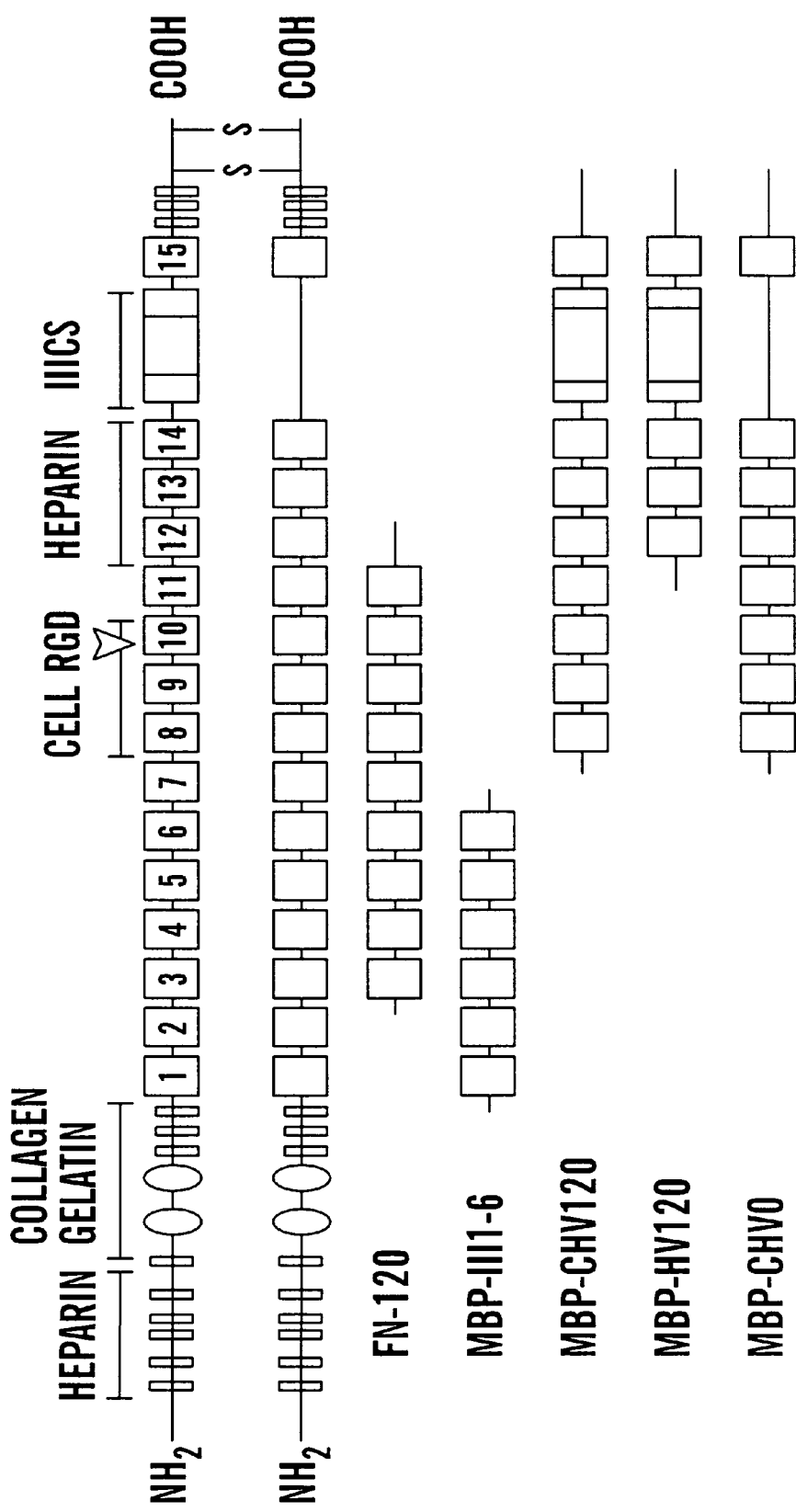
FIG. 4 illustrates the relation of the various recombinant FN proteins to the domains of FN.
Figure 5A:
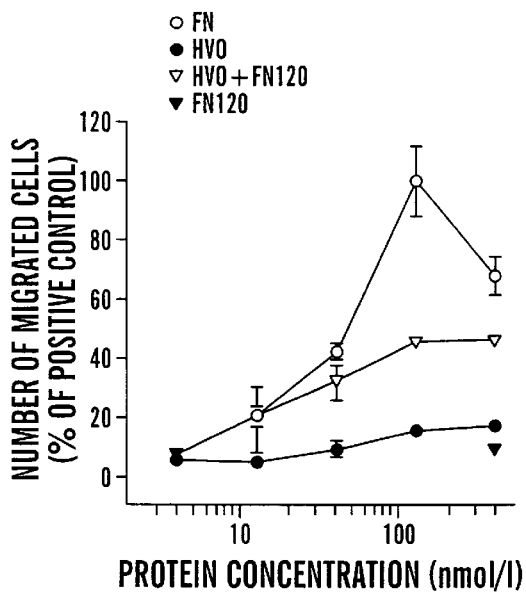
FIGS. 5A–5D illustrate the effect on cell migration of various recombinant FN proteins.
Figure 5B:
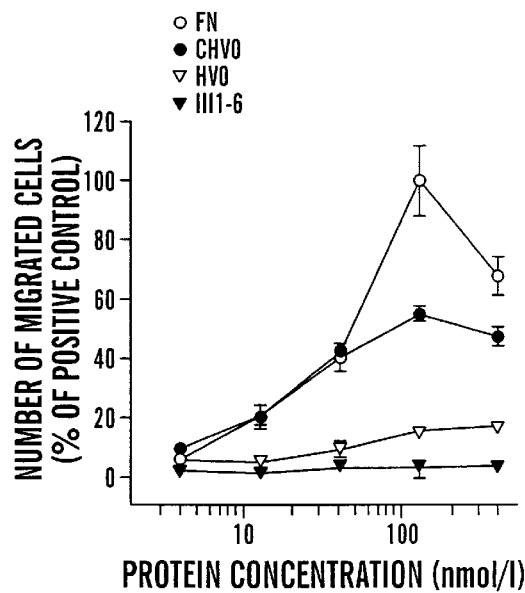

Next, the Hep II domain was examined for its ability to support migration. For this purpose a variety of recombinant FN proteins were obtained from Jean Schwartzbauer at Princeton University (Barkalow and Schwartzbauer 1991)(FIG. 4). Referring to FIG. 4, recombinant proteins are indicated by MBP. Assay plates were coated with 4 to 400 nmol/l of FN, FN-120 or recombinant proteins by drying the protein solution overnight at room temperature. The coating efficiency of all proteins was essentially the same as judged by the bicinchoninic acid protein assay (Tuszynski and Murphy 1990). A recombinant Hep II (HV0) supported migration at a level less than 20% of the migration observed on intact FN (FIG. 5A). Addition of FN-120 and HV0 on these plates, which presented both the RGD cell-binding and heparin-binding domains, respectively, in a non contiguous array, enhanced fibroblast migration to approximately 45% of the maximum level seen with intact FN (FIG. 5A). When recombinant FN protein CHV0, which contains both the RGD cell- and the heparin-binding domains in one molecule (FIG. 4), was used to coat the plates approximately 55% of the maximum level of migration was attained (FIG. 5B). Thus, about the same level of migration occurred whether the RGD cell- and heparin-binding domains were available to the cells in contiguous, or non contiguous, arrangments. Neither the FN-120 fragment alone, nor a control recombinant peptide III1-6, containing the 1st through the 6th FN type III repeats without known cell-binding sites (FIG. 4), allowed any migration (FIG. 5A and 5B).

Figure 5C:
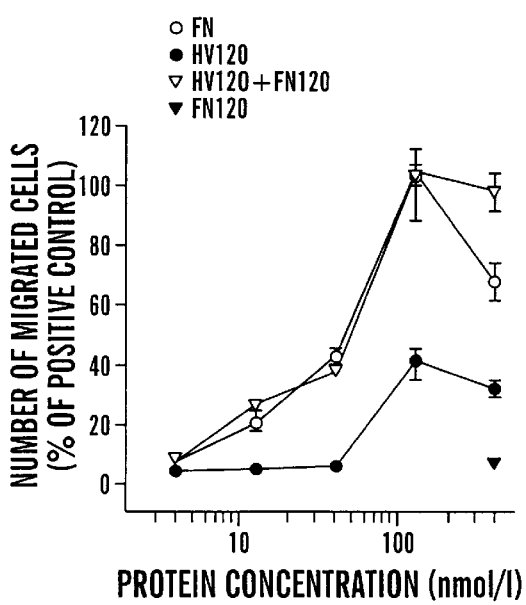
Figure 5D:
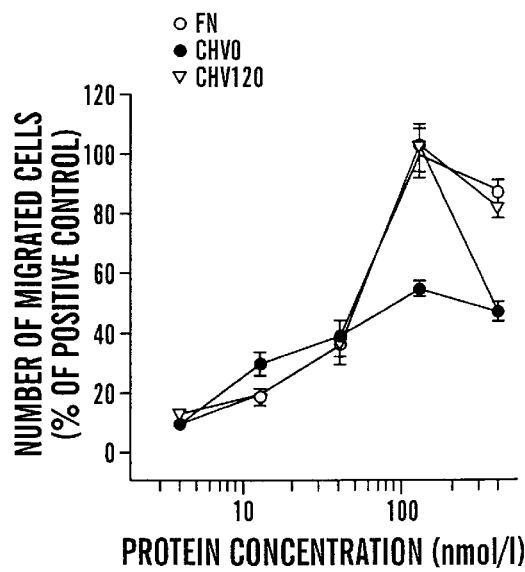

Next, experiments were conducted to examine whether the Hep II domain combined with the IIICS domain, which contains classic α4β1 binding sites, supports more migration than the Hep II domain alone. To this end, a recombinant protein HV120 containing both these domains (FIG. 4) was added to the surface of assay plates. As shown in FIG. 5C, HV120 supported 40% of the maximal migration observed with intact FN. When plates were coated with HV120, containing the heparin-binding and IIICS domains, and the FN-120 FN fragment, containing the RGD cell-binding domain, migration comparable to that on intact FN was observed (FIG. 5C). When a recombinant protein CHV120, which contains the RGD-cell binding domain, the heparin-binding domain and the IIICS domain within one molecule (FIG. 4), was used to coat assay plates, essentially the same result was obtained; that is, maximal levels of migration were seen compared to migration on intact FN (FIG. 5D).

Figure 6:
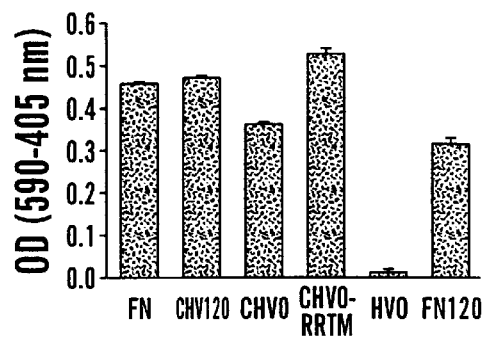
FIG. 6 illustrates the levels of fibroblast adhesion for various recombinant FN proteins.

Migration supported with CHV0 (about 55% maximum, FIG. 5B) was completely abolished if the arginine-pair XX in the 13th type III FN repeat of the Hep II domain was mutated to uncharged amino acids (CHV0-RR-TM) as previously described (Barkalow and Schwartzbauer 1991). In contrast, CHV0-RR-TM supported fibroblast adhesion at levels comparable to intact FN, CHV120 and CHV0 (FIG. 6).

Figure 7:
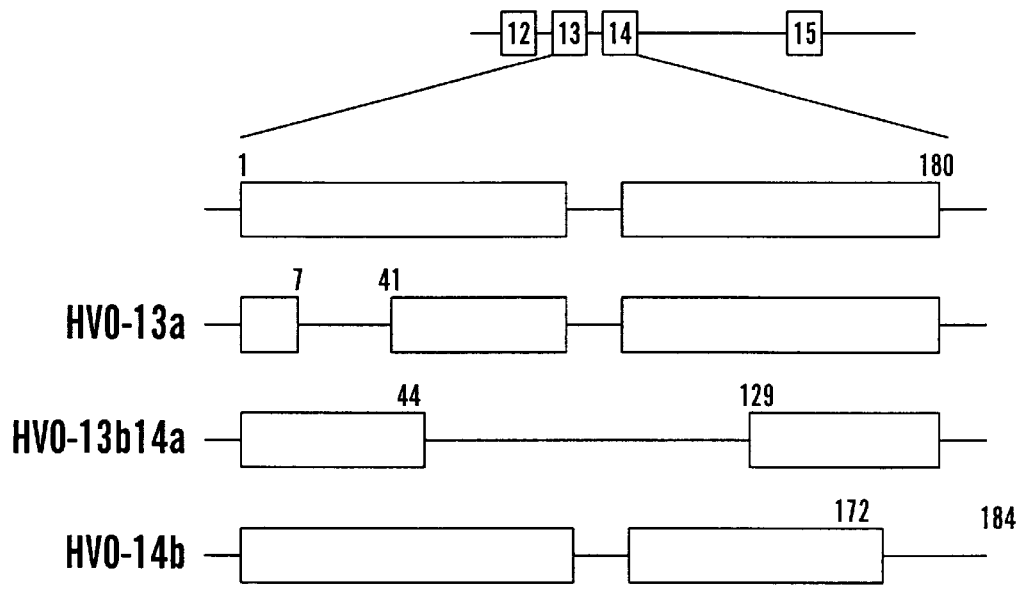
FIG. 7 illustrates the relation of various deletion mutants of the Hep II domain to the Hep II domain of FN.

These results lead to the conclusion that short, specific sequences within the Hep II domain are absolutely necessary for cell motility. To address this, deletion mutants of the Hep II domain were investigated (HV0-13a, HV0-13b14a, and HV0-14b, which were missing selected sequences of amino acids in the 13th and 14th type III repeats as shown in FIG. 7 and previously described (Barkalow and Schwartzbauer 1991; Barkalow and Schwartzbauer 1994)). HV0 and its mutants supported little migration by themselves at concentrations up to 400 nmol/l (Table 1). Furthermore, the addition of FN-120 along with the Hep II deletion mutants to the assay plates did not enhance migration (Table 1). In contrast, when FN-120 was added to the assay plates in combination with the entire recombinant Hep II domain (HV0) migration was enhanced (Table 1 and FIG. 5A). These results confirm the conclusion that subdomains within the Hep II domain are required for optimal cell migration.

Figure 8:
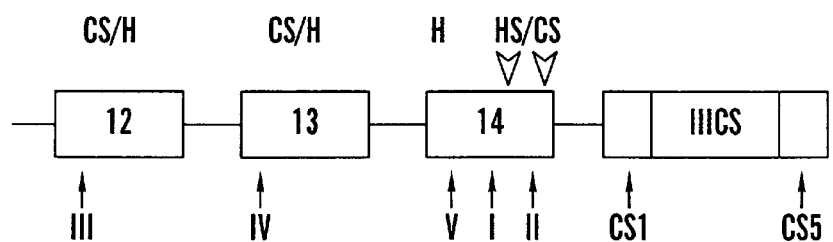
FIG. 8 illustrates the relation of various synthetic peptides to the Hep II and IIICS domains of FN.

To further define which Hep II and IIICS subdomains are involved in fibroblast migration on FN, synthetic peptides previously shown to be active in cell adhesion were manufactured from sequences in the 12th, 13th, and 14th FN type III repeats (peptides I, II, III, IV, and V)(McCarthy et al. 1988; McCarthy et al. 1990; Drake et al. 1993; Mooradian et al. 1993) and the IIICS segment (CS1 and CS5)(Humphries et al. 1987; Komoriya et al. 1991; Mould et al. 1991)(FIG. 8). FN peptide I (FN-C/HI; SEQ ID NO:6:), peptide V (FN-C/HV; SEQ ID NO:10:), CS1 (SEQ ID NO:3:), and CS1i (i=inactive, SEQ ID NO:12:) were purchased from Peninsula Laboratories Inc. (Belmont, Calif.). FN peptide II (FN-C/HII; SEQ ID NO:7:), peptide III (FN-C/HIII; SEQ ID NO:8:), peptide IV (FN-C/HIV; SEQ ID NO:9:), and CS5 (SEQ ID NO:5:) were synthesized by SynPep (Dublin, Calif.). The purity of all peptides was higher than 97%.

Figure 9A:
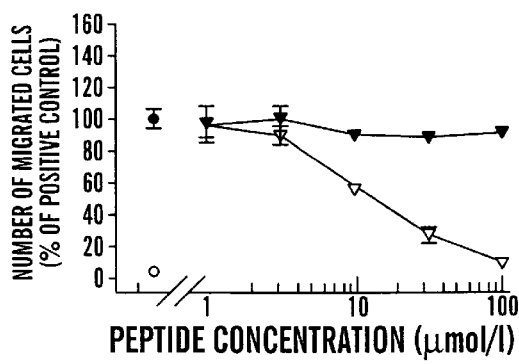
FIGS. 9A–9H illustrate the effect on cell migration of various synthetic peptides.
Figure 9B:
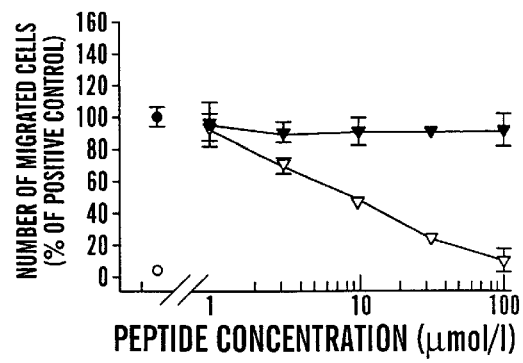
Figure 9C:
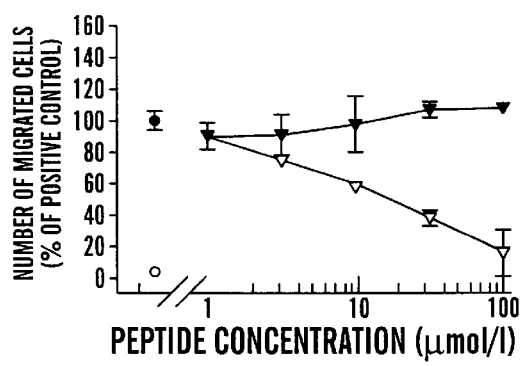
Figure 9D:
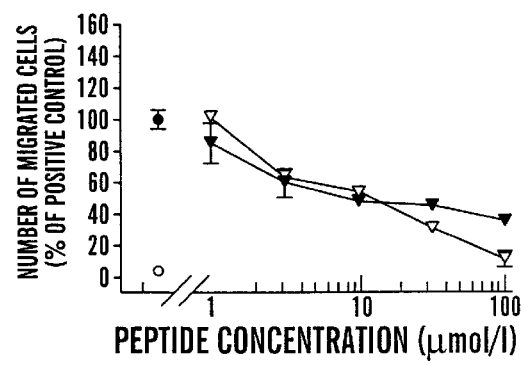
Figure 9E:
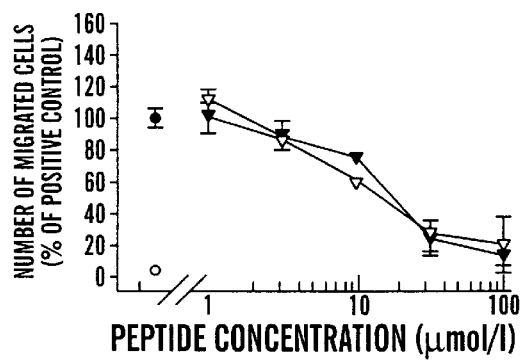
Figure 9F:
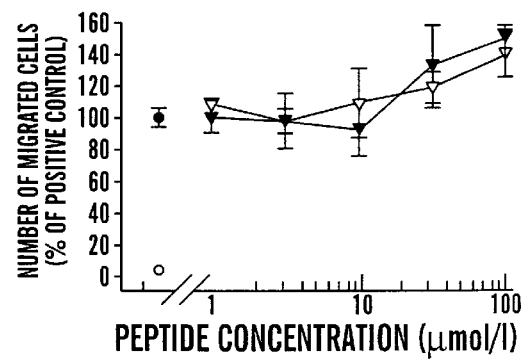
Figure 9G:
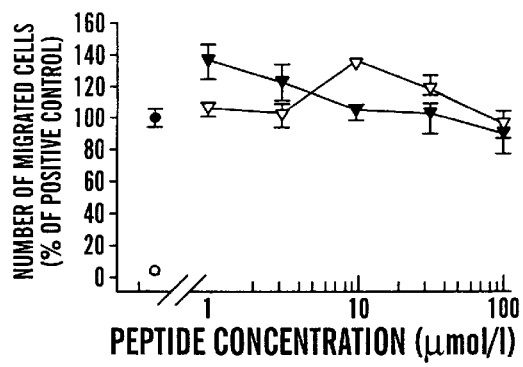
Figure 9H:
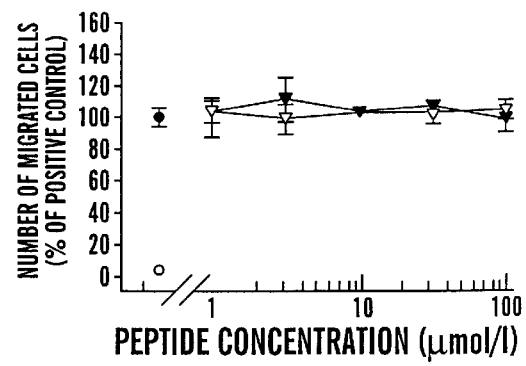

When added to the outmigration assay, peptides III (FIG. 9A), IV (FIG. 9B), V (FIG. 9C), I (FIG. 9D), and II (FIG. 9E) inhibited the migration of fibroblasts onto dried FN in a dose-dependent manner. CS1 (FIG. 9F) had a slightly enhancing effect in the higher concentrations while CS5 did not influence the migration at the tested concentrations (FIG. 9G). A control scrambled peptide of CS1 (CS1i), did not influence migration (FIG. 9H). To determine whether the observed effect of synthetic peptides on the migration was specific for FN, collagen coated assay plates were substituted for FN coated plates. Peptides III (FIG. 9A), IV (FIG. 9B), and V (FIG. 9C) had no effect on migration over collagen while peptides I and II (FIG. 9D and 9E, respectively) had an inhibitory effect in a dose-dependent manner. CS5 enhanced the migration at higher concentrations (FIG. 9G) while CS1i did not influence the activity (FIG. 9H).

To determine whether the results obtained from the two-dimensional outmigration assay related to more complex, 3-dimensional transmigration, the same synthetic peptides were added to the fibrin/FN gel in the transmigration assay. Most peptides gave essentially the same results. In aggregate these data demonstrate that 3 major domains of FN are required for fibroblast migration.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

|  | no additional protein added to plates | +FN-120 |
|---|---|---|
| FN[a] | 100 ± 2.7[b] |  |
| HV0 | 15.3 ± 1.1[c] | 45.4 ± 1.1 |
| HV0-13a | 23.3 ± 1.7 | 23.3 ± 2.2 |

TABLE 1-continued

| | no additional protein added to plates | +FN-120 |
|---|---|---|
| HV0-13b14a | 6.3 ± 2.4 | 8.7 ± 4.8 |
| HV0-14b | 20.1 ± 2.0 | 15 ± 3.7 |

[a]All proteins and peptides were assayed at concentrations from 3 to 400 nmol/l, however, maximum fibroblast migration was observed when 120 nmol/l protein was added to assay plates. Therefore, the data shown were acquired from plates coated with 120 nmol/l FN, recombinant peptides or FN-120.
[b]Fibroblast migration on fibronectin (FN) was normalized to 100%.
[c]Data are presented as mean ± SD percent migration of that observed on FN. All conditions were run in triplicate.

REFERENCES

Abraham, J. A., and Klagsbrun, M., in "The Molecular and Cellular Biology of Wound Repair", 2d edition, Clark, R. A. F., ed, Plenum Press, New York, N.Y. (1996).

Barkalow, F. J., and Schwarzbauer, J. E., J Biol Chem 266(12):7812–7818 (1991).

Barkalow, F. J., and Schwarzbauer, J. E., J Biol Chem 269(6):3957–3962 (1994).

Bartold, P. M., and Raben, A., J Periodontal Research 31(3):205–216 (1996).

Bergstrom, N., et al., "Treatment of Pressure Ulcers", U.S. Department of Health and Human Services, Clinical Practice Guideline, Vol. 15, Rockville, Md. (1994).

Borgognoni, L., et al., Euro J Dermatology 6(2):127–131 (1996).

Boyce, S. T., et al., Ann Surg 222:743–752 (1995).

Brown, G. L., et al., N Eng J Med 321:76–79 (1989).

Callam, M. J., et al., Br med J 294:1389–1391 (1987).

Devries, H. J. C., et al., Laboratory Investigation 73(4):532–540 (1995).

Drake, S. L., et al., J Biol Chem 268(21):15859–15867 (1993).

Ellis, D. L., and Yannas, I. V., Biomaterials 17(3):291–299 (1996).

Gailit, J., et al., J Invest Dermat 100:323–328 (1993).

Greiling, D., and Clark, R. A. F., J Cell Sci 110:861–870 (1997).

Heldin, C. -H., and Westermark, B., in "The Molecular and Cellular Biology of Wound Repair", 2d edition, Clark, R. A. F., ed, Plenum Press, New York, N.Y., pp 249–274 (1996).

Henke, C. A., et al., J Clin Investigation 97(11):2541–2552 (1996).

Humphries, M. J., et al., J Biol Chem 262:6886–6892 (1987).

Kartha, S., and Toback, F. G., J Clinical Investigation 90(1):288–292 (1992).

Kishida, A., et al., Biomaterials 13(13):924–930 (1992).

Komoriya, A., et al., J Biol Chem 266(23):15075–15079 (1991).

Kratz, G., et al., Scandinavian J of Plastic and Reconstructive Surgery and Hand Surgery 31(2):119–123 (June 1997).

Lamme, E. N., et al., J Histochemistry and Cytochemistry 44(11):1311–1322 (1996).

Lees, T. A., and Lambert, D., Br J Surg 79:1032–1034 (1992).

Lindholm, C., et al., Acta Derm Venereol (Stockh) 72:227–230 (1992).

McCarthy, J. B., et al., Biochem 27:1380–1388 (1988).

McCarthy, J. B., et al., J Biol Chem 110:777–787 (1990).

Medical Data International, Inc., "Wound Card in the US: Emerging trends, management and new product development" (1993).

Mooradian, D. L., et al., Invest Ophthalmol Vis Sci 34(1):153–164 (1993).

Mould, A. P., et al., J Biol Chem 266:3579–3585 (1991).

Nakamura, M., et al., Experimental Eye Research 64(6):1043–1050 (1997).

Nanney, L. B., and King, L. E., in "The Molecular and Cellular Biology of Wound Repair", 2d edition, Clark, R. A. F., ed, Plenum Press, New York, N.Y., pp 171–194 (1996).

Ortonne, J. P., J Dermatological Treatment 7(2):75–81 (1996).

Phillips, L. G., et al., Ann Plast Surg 31:331–334 (1993).

Phillips, T. J., and Dover, J. S., J Am Acad Dermatol 25:965–987 (1991).

Roberts, A. B., and Sporn, M. B., in "The Molecular and Cellular Biology of Wound Repair", 2d edition, Clark, R. A. F., ed, Plenum Press, New York, N.Y., pp 275–310 (1996).

Robson, M. C., et al., Ann Surg 216:401–406 (1992a).

Robson, M. C., et al., Ann Plast Surg 29:193–201 (1992b).

Schor, S. L., et al., J Cell Science 109:2581–2590 (1996).

Schultz, G., et al., Acta Ophthalmologica 70(S202):60–66 (1992).

Sponsel, H. T., et al., Am J Physiology 267(2):F257–264 (1994).

Steed, D. L., et al., Diabetes Care 18(1):39–46 (1995).

Tuszynski, G. P., and Murphy, A., Anal Biochem 184:189–191 (1990).

Wikner, N. E., and Clark, R. A. F., Methods in Enzymology 162:214–222 (1988).

Yamada, N., et al., Scandinavian J of Plastic and Reconstructive Surgery and Hand Surgery 29(3):211–219 (1995).

Yamada, K. M., and Clark, R. A. F., in "The Molecular and Cellular Biology of Wound Repair", 2d edition, Clark, R. A. F., ed, Plenum Press, New York, N.Y., pp 51–93 (1996).

---

What is claimed is:

1. An extracellular matrix comprising a non-contiguous array of peptides from at least three fibronectin domains in a backbone matrix, the three fibronectin domains being the cell binding domain, the IIICS domain, and the heparin II binding domain.

2. The extracellular matrix of claim 1 wherein one of the non-contiguous array of peptides is from the cell binding domain and includes the amino acid sequence SEQ ID NO:1.

3. The extracellular matrix of claim 1 wherein one of the non-contiguous array of peptides is from the cell binding domain and includes the amino acid sequence SEQ ID NO:2.

4. The extracellular matrix of claim 1 wherein one of the non-contiguous array of peptides is from the IIICS domain and includes the amino acid sequence SEQ ID NO:3.

5. The extracellular matrix of claim 1 wherein one of the non-contiguous array of peptides is from the IIICS domain and is designated CS1 and has an amino acid sequence as shown in SEQ ID NO:4.

6. The extracellular matrix of claim 1 wherein one of the non-contiguous array of peptides is from the IIICS domain and is designated CS5 and has an amino acid sequence as shown in SEQ ID NO:5.

7. The extracellular matrix of claim 1 wherein one of the non-contiguous array of peptides is from the heparin II binding domain and is designated H-I and has an amino acid sequence as shown in SEQ ID NO:6.

8. The extracellular matrix of claim 1 wherein one of the non-contiguous array of peptides is from the heparin II binding domain and is designated H-II and has an amino acid sequence as shown in SEQ ID NO:7.

9. The extracellular matrix of claim 1 wherein one of the non-contiguous array of peptides is from the heparin II binding domain and is designated H-III and has an amino acid sequence as shown in SEQ ID NO:8.

10. The extracellular matrix of claim 1 wherein one of the non-contiguous array of peptides is from the heparin II binding domain and is designated H-IV and has an amino acid sequence as shown in SEQ ID NO:9.

11. The extracellular matrix of claim 1 wherein one of the non-contiguous array of peptides is from the heparin II binding domain and is designated H-V and has an amino acid sequence as shown in SEQ ID NO:10.

12. The extracellular matrix of claim 1 wherein one of the non-contiguous array of peptides is from the heparin II binding domain and has an amino acid sequence as shown in SEQ ID NO:11.

13. The extracellular matrix of claim 1 wherein the backbone matrix comprises hyaluronic acid.

14. The extracellular matrix of claim 1 wherein the backbone matrix comprises polyethylene glycol.

15. The extracellular matrix of claim 1 wherein the backbone matrix comprises poly-L-glycol.

16. The extracellular matrix of claim 1 wherein the backbone matrix comprises poly-L-lactate.

17. The extracellular matrix of claim 1 wherein the non-contiguous array of peptides are conjugated to the backbone matrix.

18. The extracellular matrix of claim 17 wherein the non-contiguous array of peptides are conjugated to the backbone matrix using a heterobifunctional crosslinking reagent.

19. The extracellular matrix of claim 17 wherein the amino terminal amino acid of the non-contiguous array of peptides is altered to allow conjugation to the backbone matrix.

20. A method of enhancing wound healing which comprises applying the extracellular matrix of claim 1 to a wound.

21. The extracellular matrix of claim 1 further comprising one or more additional peptides from one or more of the three fibronectin domains.

* * * * *